United States Patent [19]
Geiszler

[11] 3,974,279
[45] Aug. 10, 1976

[54] N,N'-BIS-(6-AMINO)-4,4-HEXAMETHYLENEDIAMINO QUINALDINE DIHYDROCHLORIDE AS AN ANTI-L-1210 LYMPHOID AND P388 LYMPHOCYTIC LEUKEMIA AGENT

[75] Inventor: Adolph Oscar Geiszler, Mundelein, Ill.

[73] Assignee: Abbott Laboratories, North Chicago, Ill.

[22] Filed: Sept. 23, 1974

[21] Appl. No.: 508,386

Related U.S. Application Data

[63] Continuation-in-part of Ser. No. 370,498, June 15, 1973, abandoned, which is a continuation-in-part of Ser. No. 316,934, Dec. 20, 1972, abandoned, which is a continuation-in-part of Ser. No. 281,257, Aug. 16, 1972, abandoned.

[52] U.S. Cl. .............................. 424/258
[51] Int. Cl.$^2$ ......................... A61K 31/47
[58] Field of Search ..................... 424/258

[56] References Cited
UNITED STATES PATENTS
3,026,322  3/1962  Schook .................... 260/286

Primary Examiner—Jerome D. Goldberg
Attorney, Agent, or Firm—Robert L. Niblack; Vincent A. Mallare

[57] ABSTRACT

A method of prolonging survival time of mammalian cancer hosts and/or ameliorating tumor growth comprising administering a therapeutically effective amount of N,N'-bis-(6-amino)-4,4-hexamethylenediamino quinaldine dihydrochloride.

3 Claims, No Drawings

N,N'-BIS-(6-AMINO)-4,4-HEXAMETHYLENEDIAMINO QUINALDINE DIHYDROCHLORIDE AS AN ANTI-L-1210 LYMPHOID AND P388 LYMPHOCYTIC LEUKEMIA AGENT

CROSS-REFERENCE TO RELATED APPLICATIONS

This application is a continuation-in-part of co-pending application 370,498, filed June 15, 1973, now abandoned which was a continuation-in-part of Ser. No. 316,934, filed Dec. 20, 1972, now abandoned, which was a continuation-in-part of Ser. No. 281,257, filed Aug. 16, 1972, now abandoned.

This invention relates to a method of prolonging the survival time of mammalian cancer hosts. More particularly, this invention relates to a method of prolonging the survival time of mammalian 1210 lymphoid and P 388 lymphocytic leukemia cancer hosts comprising the administration of the compound, N,N-bis-(6-amino)-4,4-hexamethylenediamino quinaldine dihydrochloride or a pharmaceutically acceptable acid addition salt thereof to the host.

The compound useful in the practice of this invention, N,N'-bis-(6-amino)-4,4-hexamethylenediamino quinaldine dihydrochloride, is represented by the structure

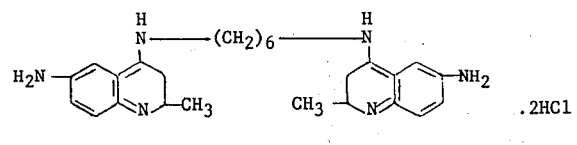

The compound can be prepared according to the method set forth in example 8 of U.S. Pat. No. 3,026,322.

N,N'-bis-(6-amino)-4,4-hexamethylenediamino quinaldine dihydrochloride and the free base have been reported to be active as trypanosides. It has now unexpectedly been found that the compound exhibits antineoplastic activity in test animals.

In the practice of this invention, N,N'-bis-(6-amino)-4,4-hexamethylenediamino quinaldine dihydrochloride is administered to mammalian cancer hosts in parenteral dosages of from 30 to 600 mg./kg. of host weight. It is well understood by those skilled in the art that dosage regimens are often complex and may vary from host to host. Generally speaking however, the drug is administered daily in single dosages for 10 to 20 days. Maintenance dosages may be administered weekly or monthly depending on the progress of the host. The following example further illustrates this invention:

EXAMPLE 1

N,N'-bis-(6-amino)-4,4-hexamethylenediamino quinaldine dihydrochloride was first evaluated in $BDF_1$ mice against L-1210 lymphoid leukemia. $10^5$ L-1210 lymphoid leukemia cells were injected into the mice. The cells were placed in either acetone, methylcellulose or saline with Tween-80. Counting the day of cell implantation as day 0, test mice received daily single injections of drug beginning on day 1 and for 3 or 9 days. The mice were evaluated on days 20 or 30. Evaluation is based on survival. In general, a minimal increase in survival of treated animals over controls resulting in a T-C $\geq$ 125% is considered significant.

The following Tables I and Ia summarize the data:

Table I

Activity of N,N'-Bis-(6-amino)-4,4-Hexamethylene-Diaminoquinaldine Against L-1210 Lymphoid Leukemia in $BDF_1$ Mice

| Dose (i.p.) | Vehicle | No. of Injec. | Day of Eval. | Survivors ( ) of ( ) | Control Body Wt. Change | Animal Wt. Diff.(T—C) | Tumor Evaluation Test | Tumor Evaluation Control | Percent T/C % |
|---|---|---|---|---|---|---|---|---|---|
| 300 | C | 9 | 30 | 5/6 | 0.2 | −5.0 | 6.0 | 9.5 | — |
| 150 | C | 9 | 30 | 6/6 | 0.2 | −5.0 | 15.3 | 9.5 | 161 |
| 75.0 | C | 9 | 30 | 6/6 | 0.2 | −3.4 | 15.2 | 9.5 | 160 |
| 37.5 | C | 9 | 30 | 5/6 | 0.2 | −2.11 | 12.0 | 9.5 | 134 |
| 400 | J | 3 | 30 | 6/6 | 1.5 | −4.9 | 12.8 | 8.6 | 148 |
| 200 | J | 3 | 30 | 6/6 | 1.5 | −1.9 | 11.0 | 8.6 | 127 |
| 100 | J | 3 | 30 | 6/6 | 1.5 | −1.4 | 9.7 | 8.6 | 112 |
| 300 | 2 | 3 | 20 | 6/6 | 1.1 | −3.3 | 9.0 | 8.9 | 101 |
| 200 | 2 | 3 | 20 | 6/6 | 1.1 | −3.2 | 11.7 | 8.9 | 131 |
| 133 | 2 | 3 | 20 | 5/6 | 1.1 | −1.0 | 11.2 | 8.9 | 125 |
| 37.5 | C | 9 | 30 | 5/6 | 0.2 | −2.1 | 12.8 | 9.5 | 134 |
| 75.0 | C | 9 | 30 | 6/6 | 0.2 | −3.4 | 15.2 | 9.5 | 160 |
| 150.0 | C | 9 | 30 | 6/6 | 0.2 | −5.0 | 15.3 | 9.5 | 161 |
| 300.0 | C | 9 | 30 | 5/6 | 0.2 | −5.0 | 6.0 | 9.5 | — |
| 16.5 | 2 | 9 | 30 | 6/6 | 1.2 | −0.9 | 10.2 | 8.6 | 127 |
| 24.7 | 2 | 9 | 30 | 6/6 | 1.2 | −1.5 | 11.0 | 8.6 | 118 |
| 600 | T | 3 | 30 | 6/6 | 2.7 | −5.9 | 18.7 | 9.4 | 198 |
| 400 | T | 3 | 30 | 6/6 | 2.7 | −3.4 | 6.0 | 9.4 | — |
| 266 | T | 3 | 30 | 6/6 | 2.7 | −3.2 | 10.5 | 9.4 | 111 |
| 180 | T | 3 | 30 | 6/6 | 2.7 | −3.7 | 14.3 | 9.4 | 152 |
| 600 | M | 3 | 30 | 6/6 | 1.1 | −3.1 | 17.2 | 8.7 | 197 |
| 400 | M | 3 | 30 | 5/6 | 1.1 | −3.5 | 15.0 | 8.7 | 172 |
| 266 | M | 3 | 30 | 4/6 | 1.1 | −3.1 | 12.8 | 8.7 | 147 |
| 180 | M | 3 | 30 | 5/6 | 1.1 | −2.3 | 14.0 | 8.70 | 160 |
| 300 | 2 | 9 | 30 | 4/6 | 1.2 | −4.1 | 8.0 | 9.5 | — |
| 150 | 2 | 9 | 30 | 4/6 | 1.2 | −4.1 | 6.0 | 9.5 | — |
| 75.0 | 2 | 9 | 30 | 6/6 | 1.2 | −2.7 | 17.3 | 9.5 | 182 |
| 37.5 | 2 | 9 | 30 | 6/6 | 1.2 | −2.5 | 15.6 | 9.5 | 164 |
| 18.0 | 2 | 9 | 30 | 6/6 | 1.2 | − .7 | 12.5 | 9.5 | 131 |
| 300 | T | 9 | 60 | 10/10 | 2.3 | −6.6 | 8.6 | 9.1 | 94 |
| 150 | T | 0 | 60 | 10/10 | 2.3 | −5.9 | 9.3 | 9.1 | 102 |
| 75.0 | T | 9 | 60 | 10/10 | 2.3 | −5.0 | 13.7 | 9.1 | 150 |
| 37.5 | T | 9 | 60 | 10/10 | 2.3 | −4.4 | 16.1 | 9.1 | 176 |

Table I-continued
Activity of N,N'-Bis-(6-amino)-4,4-Hexamethylene-Diaminoquinaldine Against L-1210 Lymphoid Leukemia in BDF$_1$ Mice

| Dose (i.p.) | Vehicle | No. of Injec. | Day of Eval. | Survivors ( ) of ( ) | Control Body Wt. Change | Animal Wt. Diff.(T−C) | Tumor Evaluation Test | Tumor Evaluation Control | Percent T/C % |
|---|---|---|---|---|---|---|---|---|---|
| 18.7 | T | 9 | 60 | 10/10 | 2.3 | −1.8 | 13.9 | 9.1 | 152 |
| 9.30 | T | 9 | 60 | 10/10 | 2.3 | −1.1 | 12.3 | 9.1 | 135 |
| 4.70 | T | 9 | 60 | 10/10 | 2.3 | − .3 | 10.7 | 9.1 | 117 |
| 300 | C | 9 | 30 | 5/6 | .2 | −5.0 | 6.0 | 9.5 | — |
| 150 | C | 9 | 30 | 6/6 | .2 | −5.0 | 15.3 | 9.5 | 161 |
| 75.0 | C | 9 | 30 | 6/6 | .2 | −3.4 | 15.2 | 9.5 | 160 |
| 37.5 | C | 9 | 30 | 5/6 | .2 | −2.1 | 12.8 | 9.5 | 134 |
| 24.7 | 2 | 9 | 30 | 6/6 | 1.2 | −1.5 | 11.0 | 8.6 | 127 |
| 16.5 | 2 | 9 | 30 | 6/6 | 1.2 | − .9 | 10.2 | 8.6 | 118 |
| 600 | T | 3 | 30 | 6/6 | 2.7 | −5.9 | 18.7 | 9.4 | 198 |
| 400 | T | 3 | 30 | 6/6 | 2.7 | −3.4 | 6.0 | 9.4 | — |
| 266 | T | 3 | 30 | 6/6 | 2.7 | −3.2 | 10.5 | 9.4 | 111 |
| 180 | T | 3 | 30 | 6/6 | 2.7 | −3.7 | 14.3 | 9.4 | 152 |
| 600 | M | 3 | 30 | 6/6 | 1.1 | −3.1 | 17.2 | 8.7 | 197 |
| 400 | M | 3 | 30 | 5/6 | 1.1 | −3.5 | 15.0 | 8.7 | 172 |
| 266 | M | 3 | 30 | 4/6 | 1.1 | −3.1 | 12.8 | 8.7 | 147 |
| 180 | M | 3 | 30 | 5/6 | 1.1 | −2.3 | 14.0 | 8.7 | 160 |
| 300 | 2 | 9 | 30 | 4/6 | 1.2 | −4.1 | 8.0 | 9.5 | — |
| 150 | 2 | 9 | 30 | 4/6 | 1.2 | −4.1 | 6.0 | 9.5 | — |
| 75.0 | 2 | 9 | 30 | 6/6 | 1.2 | −2.7 | 17.3 | 9.5 | 182 |
| 37.5 | 2 | 9 | 30 | 6/6 | 1.2 | −2.5 | 15.6 | 9.5 | 164 |
| 18.0 | 2 | 9 | 30 | 6/6 | 1.2 | − .7 | 12.5 | 9.5 | 131 |
| 300 | C | 9 | 30 | 5/6 | .2 | −5.0 | 6.0 | 9.5 | — |
| 150 | C | 9 | 30 | 6/6 | .2 | −5.0 | 15.3 | 9.5 | 161 |
| 75.0 | C | 9 | 30 | 6/6 | .2 | −3.4 | 15.2 | 9.5 | 160 |
| 37.5 | C | 9 | 30 | 5/6 | .2 | −2.1 | 12.8 | 9.5 | 134 |
| 24.7 | 2 | 9 | 30 | 6/6 | 1.2 | −1.5 | 11.0 | 8.6 | 127 |
| 16.5 | 2 | 9 | 30 | 6/6 | 1.2 | − .9 | 10.2 | 8.6 | 118 |
| 600 | T | 3 | 30 | 6/6 | 2.7 | −5.9 | 18.7 | 9.4 | 198 |
| 400 | T | 3 | 30 | 6/6 | 2.7 | −3.4 | 6.0 | 9.4 | — |
| 266 | T | 3 | 30 | 6/6 | 2.7 | −3.2 | 10.5 | 9.4 | 111 |
| 180 | T | 3 | 30 | 6/6 | 2.7 | −3.7 | 14.3 | 9.4 | 152 |
| 300 | C | 9 | 30 | 5/6 | .2 | −5.0 | 6.0 | 9.5 | — |
| 150 | C | 9 | 30 | 6/6 | .2 | −5.0 | 15.3 | 9.5 | 161 |
| 75.0 | C | 9 | 30 | 6/6 | .2 | −3.4 | 15.2 | 9.5 | 160 |
| 37.5 | C | 9 | 30 | 5/6 | .2 | −2.1 | 12.8 | 9.5 | 134 |
| 24.7 | 2 | 9 | 30 | 6/6 | 1.2 | −1.5 | 11.0 | 8.6 | 127 |
| 16.5 | 2 | 9 | 30 | 6/6 | 1.2 | − .9 | 10.2 | 8.6 | 118 |
| 600 | T | 3 | 30 | 6/6 | 2.7 | −5.9 | 18.7 | 9.4 | 198 |
| 400 | T | 3 | 30 | 6/6 | 2.7 | −3.4 | 6.0 | 9.4 | — |
| 266 | T | 3 | 30 | 6/6 | 2.7 | −3.2 | 10.5 | 9.4 | 111 |
| 180 | T | 3 | 30 | 6/6 | 2.7 | −3.7 | 14.3 | 9.4 | 152 |
| 600 | M | 3 | 30 | 6/6 | 1.1 | −3.1 | 17.2 | 8.7 | 197 |
| 400 | M | 3 | 30 | 5/6 | 1.1 | −3.5 | 15.0 | 8.7 | 172 |
| 266 | M | 3 | 30 | 4/6 | 1.1 | −3.1 | 12.8 | 8.7 | 147 |
| 180 | M | 3 | 30 | 5/6 | 1.1 | −2.3 | 14.0 | 8.7 | 160 |
| 300 | C | 9 | 30 | 5/6 | .2 | −5.0 | 6.0 | 9.5 | — |
| 150 | C | 9 | 30 | 6/6 | .2 | −5.0 | 15.3 | 9.5 | 161 |
| 75.0 | C | 9 | 30 | 6/6 | .2 | −3.4 | 15.2 | 9.5 | 160 |
| 37.5 | C | 9 | 30 | 5/6 | .2 | −2.1 | 12.8 | 9.5 | 134 |
| 24.7 | 2 | 9 | 30 | 6/6 | 1.2 | −1.5 | 11.0 | 8.6 | 127 |
| 16.5 | 2 | 9 | 30 | 6/6 | 1.2 | − .9 | 10.2 | 8.6 | 118 |
| 500 | T | 7 | 30 | 6/6 | 2.7 | −5.9 | 18.7 | 9.4 | 198 |
| 400 | T | 7 | 30 | 6/6 | 2.7 | −3.4 | 6.0 | 9.4 | — |
| 266 | T | 7 | 30 | 6/6 | 2.7 | −3.2 | 10.5 | 9.4 | 111 |
| 180 | T | 7 | 30 | 6/6 | 2.7 | −3.7 | 14.3 | 9.4 | 152 |
| 500 | M | 7 | 30 | 6/6 | 1.1 | −3.1 | 17.2 | 8.7 | 197 |
| 400 | M | 7 | 30 | 5/6 | 1.1 | −3.5 | 15.0 | 8.7 | 172 |
| 266 | M | 7 | 30 | 4/6 | 1.1 | −3.1 | 12.8 | 8.7 | 147 |
| 180 | M | 3 | 30 | 5/6 | 1.1 | −2.3 | 14.0 | 8.7 | 160 |
| 300 | 2 | 9 | 30 | 4/6 | 1.2 | −4.1 | 8.0 | 9.5 | — |
| 150 | 2 | 9 | 30 | 4/6 | 1.2 | −4.1 | 6.0 | 9.5 | — |
| 75.0 | 2 | 9 | 30 | 6/6 | 1.2 | −2.7 | 17.3 | 9.5 | 182 |
| 37.5 | 2 | 9 | 30 | 6/6 | 1.2 | −2.5 | 15.6 | 9.5 | 164 |
| 18.0 | 2 | 9 | 30 | 6/6 | 1.2 | − .7 | 12.5 | 9.5 | 131 |
| 300 | C | 9 | 30 | 5/6 | .2 | −5.0 | 6.0 | 9.5 | — |
| 150 | C | 9 | 30 | 6/6 | .2 | −5.0 | 15.3 | 9.5 | 161 |
| 75.0 | C | 9 | 30 | 6/6 | .2 | −3.4 | 15.2 | 9.5 | 160 |
| 37.5 | C | 9 | 30 | 5/6 | .2 | −2.1 | 12.8 | 9.5 | 134 |
| 24.7 | 2 | 9 | 30 | 6/6 | 1.2 | −1.5 | 11.0 | 8.6 | 127 |
| 16.5 | 2 | 9 | 30 | 6/6 | 1.2 | − .9 | 10.2 | 8.6 | 118 |
| 600 | 2 | 3 | 30 | 6/6 | 1.5 | −4.9 | 12.8 | 8.6 | 148 |
| 400 | 2 | 3 | 30 | 6/6 | 1.5 | −1.9 | 11.0 | 8.6 | 127 |
| 200 | 2 | 3 | 30 | 6/6 | 1.5 | −1.4 | 9.7 | 8.6 | 112 |

C = Acetone,
S = Saline,
T = Saline with Tween,
H = Hydroxypropylcellulose (HPC),
A = Alcohol
M = Methylcellulose

Table 1a

Activity of N,N'-Bis-(6-amino)-4,4-Hexamethylene-Diaminoquinaldine Against L-1210 Lymphoid Leukemia in BDF₁ Mice

| Dose (i.p.) | Vehicle | No. of Injec. | Day of Eval. | Survivors ( ) of ( ) | Control Body Wt. Change | Animal Wt. Diff.(T–C) | Tumor Evaluation Test | Tumor Evaluation Control | Percent T/C % |
|---|---|---|---|---|---|---|---|---|---|
| 300 | C | 9 | 30 | 5/6 | .2 | −5.0 | 6.0 | 9.5 | — |
| 150 | C | 9 | 30 | 6/6 | .2 | −5.0 | 15.3 | 9.5 | 161 |
| 75.0 | C | 9 | 30 | 6/6 | .2 | −3.4 | 15.2 | 9.5 | 160 |
| 37.5 | C | 9 | 30 | 5/6 | .2 | −2.1 | 12.8 | 9.5 | 134 |
| 24.7 | 2 | 9 | 30 | 6/6 | 1.2 | −1.5 | 11.0 | 8.6 | 127 |
| 16.5 | 2 | 9 | 30 | 6/6 | 1.2 | − .9 | 10.2 | 8.6 | 118 |
| 600 | T | 3 | 30 | 6/6 | 2.7 | −5.9 | 18.7 | 9.4 | 198 |
| 400 | T | 3 | 30 | 6/6 | 2.7 | −3.4 | 6.0 | 9.4 | — |
| 266 | T | 3 | 30 | 6/6 | 2.7 | −3.2 | 10.5 | 9.4 | 111 |
| 180 | T | 3 | 30 | 6/6 | 2.7 | −3.7 | 14.3 | 9.4 | 152 |
| 600 | M | 3 | 30 | 6/6 | 1.1 | −3.1 | 17.2 | 8.7 | 197 |
| 400 | M | 3 | 30 | 5/6 | 1.1 | −3.5 | 15.0 | 8.7 | 172 |
| 266 | M | 3 | 30 | 4/6 | 1.1 | −3.1 | 12.8 | 8.7 | 147 |
| 180 | M | 3 | 30 | 5/6 | 1.1 | −2.3 | 14.0 | 8.7 | 160 |
| 300 | 2 | 9 | 30 | 4/6 | 1.2 | −4.1 | 8.0 | 9.5 | — |
| 150 | 2 | 9 | 30 | 4/6 | 1.2 | −4.1 | 6.0 | 9.5 | — |
| 75.0 | 2 | 9 | 30 | 6/6 | 1.2 | −2.7 | 17.3 | 9.5 | 182 |
| 37.5 | 2 | 9 | 30 | 6/6 | 1.2 | −2.5 | 15.6 | 9.5 | 164 |
| 18.0 | 2 | 9 | 30 | 6/6 | 1.2 | − .7 | 12.5 | 9.5 | 131 |
| 300 | T | 9 | 60 | 10/10 | 2.3 | −6.6 | 8.6 | 9.1 | 94 |
| 150 | T | 9 | 60 | 10/10 | 2.3 | −5.9 | 9.3 | 9.1 | 102 |
| 75.0 | T | 9 | 60 | 10/10 | 2.3 | −5.0 | 13.7 | 9.1 | 150 |
| 37.5 | T | 9 | 60 | 10/10 | 2.3 | −4.4 | 16.1 | 9.1 | 176 |
| 18.7 | T | 9 | 60 | 10/10 | 2.3 | −1.8 | 13.9 | 9.1 | 152 |
| 9.30 | T | 9 | 60 | 10/10 | 2.3 | −1.1 | 12.3 | 9.1 | 135 |
| 4.70 | T | 9 | 60 | 10/10 | 2.3 | − .3 | 10.7 | 9.1 | 117 |
| 1024 | M | 1 | 63 | 10/10 | .0 | −3.8 | 13.0 | 10.0 | 130 |
| 512 | M | 1 | 63 | 10/10 | .0 | −2.1 | 14.0 | 10.0 | 140 |
| 256 | M | 1 | 63 | 10/10 | .0 | −3.4 | 13.0 | 10.0 | 130 |
| 128 | M | 1 | 63 | 10/10 | .0 | −2.0 | 15.0 | 10.0 | 150 |
| 64.0 | M | 1 | 63 | 10/10 | .0 | −3.8 | 13.0 | 10.0 | 130 |
| 0.00 | M | 1 | 63 | 10/10 | .0 | .6 | 10.0 | 10.0 | 100 |
| 256 | M | 9 | 63 | 9/10 | .0 | −4.1 | 9.5 | 10.0 | 95 |
| 128 | M | 9 | 63 | 10/10 | .0 | −4.1 | 10.5 | 10.0 | 105 |
| 64.0 | M | 9 | 63 | 10/10 | .0 | −3.5 | 13.5 | 10.0 | 130 |
| 32.0 | M | 9 | 63 | 10/10 | .0 | −3.8 | 14.5 | 10.0 | 145 |
| 16.0 | M | 9 | 63 | 10/10 | .0 | −2.8 | 15.5 | 10.0 | 155 |
| 8.00 | M | 9 | 63 | 10/10 | .0 | −2.6 | 14.0 | 10.0 | 140 |
| 0.00 | M | 9 | 63 | 9/10 | .0 | .6 | 9.0 | 10.0 | 90 |
| 1024 | M | 3 | 63 | 10/10 | .0 | −4.8 | 10.5 | 10.0 | 105 |
| 512 | M | 3 | 63 | 10/10 | .0 | −4.3 | 14.0 | 10.0 | 140 |
| 256 | M | 3 | 63 | 10/10 | .0 | −2.6 | 14.0 | 10.0 | 140 |
| 128 | M | 3 | 63 | 10/10 | .0 | −4.0 | 16.0 | 10.0 | 160 |
| 64.0 | M | 3 | 63 | 10/10 | .0 | −1.1 | 13.0 | 10.0 | 130 |
| 32.0 | M | 3 | 63 | 10/10 | .0 | −1.0 | 13.0 | 10.0 | 130 |
| 0.00 | M | 3 | 63 | 10/10 | .0 | −1.0 | 13.0 | 10.0 | 100 |
| 1024 | M | 2 | 63 | 10/10 | .0 | − .4 | 11.0 | 10.0 | 110 |
| 512 | M | 2 | 63 | 10/10 | .0 | −3.3 | 14.0 | 10.0 | 140 |
| 256 | M | 2 | 63 | 10/10 | .0 | −2.5 | 15.5 | 10.0 | 155 |
| 128 | M | 2 | 63 | 10/10 | .0 | −2.9 | 15.0 | 10.0 | 150 |
| 64.0 | M | 2 | 63 | 10/10 | .0 | −2.5 | 14.5 | 10.0 | 145 |
| 32.0 | M | 2 | 63 | 10/10 | .0 | −2.8 | 13.0 | 10.0 | 130 |
| 0.00 | M | 2 | 63 | 10/10 | .0 | − .3 | 9.0 | 10.0 | 90 |
| 256 | M | 9 | 63 | 10/10 | .0 | −3.8 | 9.5 | 10.0 | 95 |
| 1.28 | M | 9 | 63 | 10/10 | .0 | −3.7 | 12.5 | 10.0 | 125 |
| 64.0 | M | 9 | 63 | 10/10 | .0 | −3.2 | 11.0 | 10.0 | 110 |
| 32.0 | M | 9 | 63 | 10/10 | .0 | −3.0 | 16.0 | 10.0 | 160 |
| 16.0 | M | 9 | 63 | 10/10 | .0 | −1.9 | 11.5 | 10.0 | 115 |
| 8.00 | M | 9 | 63 | 10/10 | .0 | −1.7 | 12.5 | 10.0 | 125 |
| 1024 | M | 3 | 63 | 10/10 | .0 | −3.8 | 12.5 | 10.0 | 125 |
| 512 | M | 3 | 63 | 10/10 | .0 | −2.7 | 14.5 | 10.0 | 145 |
| 256 | M | 3 | 63 | 10/10 | .0 | −1.6 | 14.5 | 10.0 | 145 |
| 128 | M | 3 | 63 | 10/10 | .0 | −1.8 | 12.5 | 10.0 | 125 |
| 64.0 | M | 3 | 63 | 10/10 | .0 | −2.1 | 12.0 | 10.0 | 120 |
| 1024 | M | 9 | 63 | 10/10 | .0 | −2.5 | 10.0 | 10.0 | 100 |
| 512 | M | 9 | 63 | 10/10 | .0 | −2.6 | 10.0 | 10.0 | 100 |
| 256 | M | 9 | 63 | 10/10 | .0 | −2.4 | 11.5 | 10.0 | 115 |
| 128 | M | 9 | 63 | 10/10 | .0 | −3.6 | 11.0 | 10.0 | 110 |
| 64.0 | M | 9 | 63 | 10/10 | .0 | −4.0 | 11.5 | 10.0 | 115 |
| 0.00 | M | 9 | 63 | 9/9 | .0 | −5.5 | 12.0 | 10.0 | 120 |
| 204 | M | 3 | 63 | 10/10 | .0 | −2.9 | 12.0 | 10.0 | 120 |
| 102 | M | 3 | 63 | 10/10 | .0 | −2.6 | 11.0 | 10.0 | 110 |
| 51.2 | M | 3 | 63 | 10/10 | .0 | −3.4 | 11.0 | 10.0 | 110 |
| 25.6 | M | 3 | 63 | 10/10 | .0 | −2.0 | 10.0 | 10.0 | 100 |
| 0.00 | M | 3 | 63 | 10/10 | .0 | −2.9 | 11.5 | 10.0 | 115 |
| 1024 | M | 1 | 63 | 10/10 | .0 | −3.8 | 13.0 | 10.0 | 130 |
| 512 | M | 1 | 63 | 10/10 | .0 | −2.1 | 14.0 | 10.0 | 140 |
| 256 | M | 1 | 63 | 10/10 | .0 | −3.4 | 13.0 | 10.0 | 130 |
| 128 | M | 1 | 63 | 10/10 | .0 | −2.0 | 15.0 | 10.0 | 150 |
| 64.0 | M | 1 | 63 | 10/10 | .0 | −3.8 | 13.0 | 10.0 | 130 |
| 0.00 | M | 1 | 63 | 10/10 | .0 | .6 | 10.0 | 10.0 | 100 |
| 256 | M | 9 | 63 | 9/10 | .0 | −4.1 | 9.5 | 10.0 | 95 |
| 128 | M | 9 | 63 | 10/10 | .0 | −4.1 | 10.5 | 10.0 | 105 |
| 64.0 | M | 9 | 63 | 10/10 | .0 | −3.5 | 13.0 | 10.0 | 130 |
| 32.0 | M | 9 | 63 | 10/10 | .0 | −3.8 | 14.5 | 10.0 | 145 |
| 16.0 | M | 9 | 63 | 10/10 | .0 | −2.8 | 15.5 | 10.0 | 155 |
| 8.00 | M | 9 | 63 | 10/10 | .0 | −2.6 | 14.0 | 10.0 | 140 |

Table 1a-continued

Activity of N,N'-Bis-(6-amino)-4,4-Hexamethylene-Diaminoquinaldine Against L-1210 Lymphoid Leukemia in BDF$_1$ Mice

| Dose (i.p.) | Vehicle | No. of Injec. | Day of Eval. | Survivors ( ) of ( ) | Control Body Wt. Change | Animal Wt. Diff.(T—C) | Tumor Evaluation Test | Tumor Evaluation Control | Percent T/C % |
|---|---|---|---|---|---|---|---|---|---|
| 0.00 | M | 9 | 63 | 9/10 | .0 | .6 | 9.0 | 10.0 | 90 |
| 10.24 | M | 3 | 63 | 10/10 | .0 | −4.8 | 10.5 | 10.0 | 105 |
| 512 | M | 3 | 63 | 10/10 | .0 | −4.3 | 14.0 | 10.0 | 140 |
| 256 | M | 3 | 63 | 10/10 | .0 | −2.6 | 14.0 | 10.0 | 140 |
| 128 | M | 3 | 63 | 10/10 | .0 | −4.0 | 16.0 | 10.0 | 160 |
| 64.0 | M | 3 | 63 | 10/10 | .0 | −1.1 | 13.0 | 10.0 | 130 |
| 32.0 | M | 3 | 63 | 10/10 | .0 | −1.0 | 13.0 | 10.0 | 130 |
| 0.00 | M | 3 | 63 | 10/10 | .0 | − .2 | 10.0 | 10.0 | 100 |
| 1024 | M | 2 | 63 | 10/10 | .0 | − .4 | 11.0 | 10.0 | 110 |
| 512 | M | 2 | 63 | 10/10 | .0 | −3.3 | 14.0 | 10.0 | 140 |
| 256 | M | 2 | 63 | 10/10 | .0 | −2.5 | 15.5 | 10.0 | 155 |
| 128 | M | 2 | 63 | 10/10 | .0 | −2.9 | 15.0 | 10.0 | 150 |
| 64.0 | M | 2 | 63 | 10/10 | .0 | −2.5 | 14.5 | 10.0 | 145 |
| 32.0 | M | 2 | 63 | 10/10 | .0 | −2.8 | 13.0 | 10.0 | 130 |
| 0.00 | M | 2 | 63 | 10/10 | .0 | − .3 | 9.0 | 10.0 | 90 |
| 256 | M | 9 | 63 | 10/10 | .0 | −3.8 | 9.5 | 10.0 | 95 |
| 128 | M | 9 | 63 | 10/10 | .0 | −3.7 | 12.5 | 10.0 | 125 |
| 64.0 | M | 9 | 63 | 10/10 | .0 | −3.2 | 11.0 | 10.0 | 110 |
| 32.0 | M | 9 | 63 | 10/10 | .0 | −3.0 | 16.0 | 10.0 | 160 |
| 16.0 | M | 9 | 63 | 10/10 | .0 | −1.9 | 11.5 | 10.0 | 115 |
| 8.00 | M | 9 | 63 | 10/10 | .0 | −1.7 | 12.5 | 10.0 | 125 |
| 10.24 | M | 3 | 63 | 10/10 | .0 | −3.8 | 12.5 | 10.0 | 125 |
| 512 | M | 3 | 63 | 10/10 | .0 | −2.7 | 14.5 | 10.0 | 145 |
| 256 | M | 3 | 63 | 10/10 | .0 | −1.6 | 14.5 | 10.0 | 145 |
| 128 | M | 3 | 63 | 10/10 | .0 | −1.8 | 12.5 | 10.0 | 125 |
| 64.0 | M | 3 | 63 | 10/10 | .0 | −2.1 | 12.0 | 10.0 | 120 |
| 1024 | M | 9 | 63 | 10/10 | .0 | −2.5 | 10.0 | 10.0 | 100 |
| 512 | M | 9 | 63 | 10/10 | .0 | −2.6 | 10.0 | 10.0 | 100 |
| 256 | M | 9 | 63 | 10/10 | .0 | −2.4 | 11.5 | 10.0 | 115 |
| 128 | M | 9 | 63 | 10/10 | .0 | −3.6 | 11.0 | 10.0 | 110 |
| 64.0 | M | 9 | 63 | 10/10 | .0 | −4.0 | 11.5 | 10.0 | 115 |
| 0.00 | M | 9 | 63 | 9/9 | .0 | −5.5 | 12.0 | 10.0 | 120 |
| 204 | M | 3 | 63 | 10/10 | .0 | −2.9 | 12.0 | 10.0 | 120 |
| 102 | M | 3 | 63 | 10/10 | .0 | −2.6 | 11.0 | 10.0 | 110 |
| 51.2 | M | 3 | 63 | 10/10 | .0 | −3.4 | 11.0 | 10.0 | 110 |
| 25.6 | M | 3 | 63 | 10/10 | .0 | −2.0 | 10.0 | 10.0 | 100 |
| 0.00 | M | 3 | 63 | 10/10 | .0 | −2.9 | 11.5 | 10.0 | 115 |
| 128 | M | 9 | 60 | 10/10 | 1.9 | −5.3 | 13.5 | 9.0 | 150 |
| 64.0 | M | 9 | 60 | 10/10 | 1.9 | −5.0 | 17.5 | 9.0 | 194 |
| 32.0 | M | 9 | 60 | 10/10 | 1.9 | −3.9 | 15.0 | 9.0 | 166 |
| 16.0 | M | 9 | 60 | 10/10 | 1.9 | −3.3 | 13.5 | 9.0 | 150 |
| 8.00 | M | 9 | 60 | 10/10 | 1.9 | −2.6 | 12.5 | 9.0 | 138 |
| 4.00 | M | 9 | 60 | 10/10 | 1.9 | −5.0 | 10.0 | 9.0 | 111 |
| 0.00 | M | 9 | 60 | 10/10 | 1.9 | −2.6 | 9.0 | 9.0 | 100 |
| 128 | M | 8 | 60 | 9/10 | 1.9 | −7.0 | 16.0 | 9.0 | 177 |
| 64.0 | M | 8 | 60 | 10/10 | 1.9 | −5.3 | 18.0 | 9.0 | 200 |
| 32.0 | M | 8 | 60 | 10/10 | 1.9 | −5.0 | 14.0 | 9.0 | 155 |
| 16.0 | M | 8 | 60 | 9/10 | 1.9 | −5.5 | 15.0 | 9.0 | 166 |
| 8.00 | M | 8 | 60 | 10/10 | 1.9 | −4.8 | 12.5 | 9.0 | 138 |
| 0.00 | M | 8 | 60 | 10/10 | 1.9 | − .9 | 10.0 | 9.0 | 111 |
| 128 | M | 24 | 60 | 10/10 | 1.9 | −6.5 | 11.5 | 9.0 | 127 |
| 64.0 | M | 24 | 60 | 9/10 | 1.9 | −6.2 | 13.0 | 9.0 | 144 |
| 32.0 | M | 24 | 60 | 10/10 | 1.9 | −5.2 | 18.0 | 9.0 | 200 |
| 16.0 | M | 24 | 60 | 10/10 | 1.9 | −5.0 | 17.0 | 9.0 | 188 |
| 8.00 | M | 24 | 60 | 10/10 | 1.9 | −4.4 | 14.0 | 9.0 | 155 |
| 4.00 | M | 24 | 60 | 10/10 | 1.9 | −4.6 | 9.5 | 9.0 | 105 |
| 0.00 | M | 24 | 60 | 10/10 | 1.9 | −1.3 | 11.0 | 9.0 | 122 |
| 128 | M | 16 | 60 | 10/10 | 1.9 | −5.7 | 11.0 | 9.0 | 122 |
| 64.0 | M | 16 | 60 | 10/10 | 1.9 | −6.1 | 13.5 | 9.0 | 150 |
| 32.0 | M | 16 | 60 | 10/10 | 1.9 | −5.1 | 18.0 | 9.0 | 200 |
| 16.0 | M | 16 | 60 | 10/10 | 1.9 | −4.8 | 16.0 | 9.0 | 177 |
| 8.00 | M | 16 | 60 | 10/10 | 1.9 | −5.8 | 13.0 | 9.0 | 144 |
| 4.00 | M | 16 | 60 | 10/10 | 1.9 | −5.0 | 12.5 | 9.0 | 138 |
| 0.00 | M | 16 | 60 | 10/10 | 1.9 | − .9 | 9.0 | 9.0 | 100 |
| 300 | C | 9 | 30 | 5/6 | .2 | −5.0 | 6.0 | 9.5 | 63 |
| 150 | C | 9 | 30 | 6/6 | .2 | −5.0 | 15.3 | 9.5 | 161 |
| 75.0 | C | 9 | 30 | 6/6 | .2 | −3.4 | 15.2 | 9.5 | 160 |
| 37.5 | C | 9 | 30 | 5/6 | .2 | −2.1 | 12.8 | 9.5 | 135 |
| 24.7 | 2 | 9 | 30 | 6/6 | 1.2 | −1.5 | 11.0 | 8.6 | 128 |
| 16.5 | 2 | 9 | 30 | 6/6 | 1.2 | − .9 | 10.2 | 8.6 | 119 |
| 600 | T | 3 | 30 | 6/6 | 2.7 | −5.9 | 18.7 | 9.4 | 199 |
| 400 | T | 3 | 30 | 6/6 | 2.7 | −3.4 | 6.0 | 9.4 | 64 |
| 266 | T | 3 | 30 | 6/6 | 2.7 | −3.2 | 10.5 | 9.4 | 112 |
| 180 | T | 3 | 30 | 6/6 | 2.7 | −3.7 | 14.3 | 9.4 | 152 |
| 600 | M | 3 | 30 | 6/6 | 1.1 | −3.1 | 17.2 | 8.7 | 197 |
| 400 | M | 3 | 30 | 5/6 | 1.1 | −3.5 | 15.0 | 8.7 | 172 |
| 266 | M | 3 | 30 | 4/6 | 1.1 | −3.1 | 12.8 | 8.7 | 147 |
| 180 | M | 3 | 30 | 5/6 | 1.1 | −2.3 | 14.0 | 8.7 | 160 |
| 300 | 2 | 9 | 30 | 4/6 | 1.2 | −4.1 | 8.0 | 9.5 | 84 |
| 150 | 2 | 9 | 30 | 4/6 | 1.2 | −4.1 | 6.0 | 9.5 | 63 |
| 75.0 | 2 | 9 | 30 | 6/6 | 1.2 | −2.7 | 17.3 | 9.5 | 182 |
| 37.5 | 2 | 9 | 30 | 6/6 | 1.2 | −2.5 | 15.6 | 9.5 | 164 |
| 18.0 | 2 | 9 | 30 | 6/6 | 1.2 | − .7 | 12.5 | 9.5 | 161 |
| 300 | T | 9 | 60 | 10/10 | 2.3 | −6.6 | 8.6 | 9.1 | 94 |
| 150 | T | 9 | 60 | 10/10 | 2.3 | −5.9 | 9.3 | 9.1 | 102 |
| 75.0 | T | 9 | 60 | 10/10 | 2.3 | −5.0 | 13.7 | 9.1 | 150 |
| 37.5 | T | 9 | 60 | 10/10 | 2.3 | −4.4 | 16.1 | 9.1 | 176 |

Table 1a-continued

Activity of N,N'-Bis-(6-amino)-4,4-Hexamethylene-Diaminoquinaldine Against L-1210 Lymphoid Leukemia in BDF₁ Mice

| Dose (i.p.) | Vehicle | No. of Injec. | Day of Eval. | Survivors ( ) of ( ) | Control Body Wt. Change | Animal Wt. Diff.(T−C) | Tumor Evaluation Test | Tumor Evaluation Control | Percent T/C % |
|---|---|---|---|---|---|---|---|---|---|
| 18.7 | T | 9 | 60 | 10/10 | 2.3 | −1.8 | 13.9 | 9.1 | 152 |
| 9.30 | T | 9 | 60 | 10/10 | 2.3 | −1.1 | 12.3 | 9.1 | 135 |
| 4.70 | T | 9 | 60 | 10/10 | 2.3 | − .3 | 10.7 | 9.1 | 117 |
| 300 | C | 9 | 30 | 5/6 | .2 | −5.0 | 6.0 | 9.5 | — |
| 150 | C | 9 | 30 | 6/6 | .2 | −5.0 | 15.3 | 9.5 | 161 |
| 75.0 | C | 9 | 30 | 6/6 | .2 | −3.4 | 15.2 | 9.5 | 160 |
| 37.5 | C | 9 | 30 | 5/6 | .2 | −2.1 | 12.8 | 9.5 | 134 |
| 24.7 | 2 | 9 | 30 | 6/6 | 1.2 | −1.5 | 11.0 | 8.6 | 127 |
| 16.5 | 2 | 9 | 30 | 6/6 | 1.2 | − .9 | 10.2 | 8.6 | 118 |
| 600 | T | 3 | 30 | 6/6 | 2.7 | −5.9 | 18.7 | 9.4 | 198 |
| 400 | T | 3 | 30 | 6/6 | 2.7 | −3.4 | 6.0 | 9.4 | — |
| 266 | T | 3 | 30 | 6/6 | 2.7 | −3.2 | 10.5 | 9.4 | 111 |
| 180 | T | 3 | 30 | 6/6 | 2.7 | −3.7 | 14.3 | 9.4 | 152 |
| 600 | M | 3 | 30 | 6/6 | 1.1 | −3.1 | 17.2 | 8.7 | 197 |
| 400 | M | 3 | 30 | 5/6 | 1.1 | −3.5 | 15.0 | 8.7 | 172 |
| 266 | M | 3 | 30 | 4/6 | 1.1 | −3.1 | 12.8 | 8.7 | 147 |
| 180 | M | 3 | 30 | 5/6 | 1.1 | −2.3 | 14.0 | 8.7 | 160 |
| 300 | 2 | 9 | 30 | 4/6 | 1.2 | −4.1 | 8.0 | 9.5 | — |
| 150 | 2 | 9 | 30 | 4/6 | 1.2 | −4.1 | 6.0 | 9.5 | — |
| 75.0 | 2 | 9 | 30 | 6/6 | 1.2 | −2.7 | 17.3 | 9.5 | 182 |
| 37.5 | 2 | 9 | 30 | 6/6 | 1.2 | −2.5 | 15.6 | 9.5 | 164 |
| 18.0 | 2 | 9 | 30 | 6/6 | 1.2 | − .7 | 12.5 | 9.5 | 131 |
| 300 | T | 9 | 60 | 10/10 | 2.3 | −6.6 | 8.6 | 9.1 | 94 |
| 150 | T | 9 | 60 | 10/10 | 2.3 | −5.9 | 9.3 | 9.1 | 102 |
| 75.0 | T | 9 | 60 | 10/10 | 2.3 | −5.0 | 13.7 | 9.1 | 150 |
| 37.5 | T | 9 | 60 | 10/10 | 2.3 | −4.4 | 16.1 | 9.1 | 176 |
| 18.7 | T | 9 | 60 | 10/10 | 2.3 | −1.8 | 13.9 | 9.1 | 152 |
| 9.30 | T | 9 | 60 | 10/10 | 2.3 | −1.1 | 12.3 | 9.1 | 135 |
| 4.70 | T | 9 | 60 | 10/10 | 2.3 | − .3 | 10.7 | 9.1 | 117 |
| 1024 | M | 1 | 63 | 10/10 | .0 | −3.8 | 13.0 | 10.0 | 130 |
| 512 | M | 1 | 63 | 10/10 | .0 | −2.1 | 14.0 | 10.0 | 140 |
| 256 | M | 1 | 63 | 10/10 | .0 | −3.4 | 13.0 | 10.0 | 130 |
| 128 | M | 1 | 63 | 10/10 | .0 | −2.0 | 15.0 | 10.0 | 150 |
| 64.0 | M | 1 | 63 | 10/10 | .0 | −3.8 | 13.0 | 10.0 | 130 |
| 0.00 | M | 1 | 63 | 10/10 | .0 | .6 | 10.0 | 10.0 | 100 |
| 256 | M | 9 | 63 | 9/10 | .0 | −4.1 | 9.5 | 10.0 | 95 |
| 128 | M | 9 | 63 | 10/10 | .0 | −4.1 | 10.5 | 10.0 | 105 |
| 64.0 | M | 9 | 63 | 10/10 | .0 | −3.5 | 13.0 | 10.0 | 130 |
| 32.0 | M | 9 | 63 | 10/10 | .0 | −3.8 | 14.5 | 10.0 | 145 |
| 16.0 | M | 9 | 63 | 10/10 | .0 | −2.8 | 15.5 | 10.0 | 155 |
| 8.00 | M | 9 | 63 | 10/10 | .0 | −2.6 | 14.0 | 10.0 | 140 |
| 0.00 | M | 9 | 63 | 9/10 | .0 | .6 | 9.0 | 10.0 | 90 |
| 1024 | M | 3 | 63 | 10/10 | .0 | −4.8 | 10.5 | 10.0 | 105 |
| 512 | M | 3 | 63 | 10/10 | .0 | −4.3 | 14.0 | 10.0 | 140 |
| 256 | M | 3 | 63 | 10/10 | .0 | −2.6 | 14.0 | 10.0 | 140 |
| 128 | M | 3 | 63 | 10/10 | .0 | −4.0 | 16.0 | 10.0 | 160 |
| 64.0 | M | 3 | 63 | 10/10 | .0 | −1.1 | 13.0 | 10.0 | 130 |
| 32.0 | M | 3 | 63 | 10/10 | .0 | −1.0 | 13.0 | 10.0 | 130 |
| 0.00 | M | 3 | 63 | 10/10 | .0 | − .2 | 10.0 | 10.0 | 100 |
| 1024 | M | 2 | 63 | 10/10 | .0 | − .4 | 11.0 | 10.0 | 110 |
| 512 | M | 2 | 63 | 10/10 | .0 | −3.3 | 14.0 | 10.0 | 140 |
| 256 | M | 2 | 63 | 10/10 | .0 | −2.5 | 15.5 | 10.0 | 155 |
| 128 | M | 2 | 63 | 10/10 | .0 | −2.9 | 15.0 | 10.0 | 150 |
| 64.0 | M | 2 | 63 | 10/10 | .0 | −2.5 | 14.5 | 10.0 | 145 |
| 32.0 | M | 2 | 63 | 10/10 | .0 | −2.8 | 13.0 | 10.0 | 130 |
| 0.00 | M | 2 | 63 | 10/10 | .0 | − .3 | 9.0 | 10.0 | 90 |
| 256 | M | 9 | 63 | 10/10 | .0 | −3.8 | 9.5 | 10.0 | 95 |
| 128 | M | 9 | 63 | 10/10 | .0 | −3.7 | 12.5 | 10.0 | 125 |
| 64.0 | M | 9 | 63 | 10/10 | .0 | −3.2 | 11.0 | 10.0 | 110 |
| 32.0 | M | 9 | 63 | 10/10 | .0 | −3.0 | 16.0 | 10.0 | 160 |
| 16.0 | M | 9 | 63 | 10/10 | .0 | −1.9 | 11.5 | 10.0 | 115 |
| 8.00 | M | 9 | 63 | 10/10 | .0 | −1.7 | 12.5 | 10.0 | 125 |
| 1024 | M | 3 | 63 | 10/10 | .0 | −3.8 | 12.5 | 10.0 | 125 |
| 512 | M | 3 | 63 | 10/10 | .0 | −2.7 | 14.5 | 10.0 | 145 |
| 256 | M | 3 | 63 | 10/10 | .0 | −1.6 | 14.5 | 10.0 | 145 |
| 128 | M | 3 | 63 | 10/10 | .0 | −1.8 | 12.5 | 10.0 | 125 |
| 64.0 | M | 3 | 63 | 10/10 | .0 | −2.1 | 12.0 | 10.0 | 120 |
| 1024 | M | 9 | 63 | 10/10 | .0 | −2.5 | 10.0 | 10.0 | 100 |
| 512 | M | 9 | 63 | 10/10 | .0 | −2.6 | 10.0 | 10.0 | 100 |
| 256 | M | 9 | 63 | 10/10 | .0 | −2.4 | 11.5 | 10.0 | 115 |
| 128 | M | 9 | 63 | 10/10 | .0 | −3.6 | 11.0 | 10.0 | 110 |
| 64.0 | M | 9 | 63 | 10/10 | .0 | −4.0 | 11.5 | 10.0 | 115 |
| 0.00 | M | 9 | 63 | 9/9 | .0 | −5.5 | 12.0 | 10.0 | 120 |
| 204 | M | 3 | 63 | 10/10 | .0 | −2.9 | 12.0 | 10.0 | 120 |
| 102 | M | 3 | 63 | 10/10 | .0 | −2.6 | 11.0 | 10.0 | 110 |
| 51.2 | M | 3 | 63 | 10/10 | .0 | −3.4 | 11.0 | 10.0 | 110 |
| 25.6 | M | 3 | 63 | 10/10 | .0 | −2.0 | 10.0 | 10.0 | 100 |
| 0.00 | M | 3 | 63 | 10/10 | .0 | −2.9 | 11.5 | 10.0 | 115 |
| 128 | M | 9 | 60 | 10/10 | 1.9 | −5.3 | 13.5 | 9.0 | 150 |
| 64.0 | M | 9 | 60 | 10/10 | 1.9 | −5.0 | 17.5 | 9.0 | 194 |
| 32.0 | M | 9 | 60 | 10/10 | 1.9 | −3.9 | 15.0 | 9.0 | 166 |
| 16.0 | M | 9 | 60 | 10/10 | 1.9 | −3.3 | 13.5 | 9.0 | 150 |
| 8.00 | M | 9 | 60 | 10/10 | 1.9 | −2.6 | 12.5 | 9.0 | 138 |
| 4.00 | M | 9 | 60 | 10/10 | 1.9 | −5.0 | 10.0 | 9.0 | 111 |
| 0.00 | N | 9 | 60 | 10/10 | 1.9 | −2.6 | 9.0 | 9.0 | 100 |
| 128 | M | 8 | 60 | 9/10 | 1.9 | −7.0 | 16.0 | 9.0 | 177 |
| 64.0 | M | 8 | 60 | 10/10 | 1.9 | −5.3 | 18.0 | 9.0 | 200 |

Table 1a-continued

Activity of N,N'-Bis-(6-amino)-4,4-Hexamethylene-Diaminoquinaldine Against L-1210 Lymphoid Leukemia in BDF₁ Mice

| Dose (i.p.) | Vehicle | No. of Injec. | Day of Eval. | Survivors ( ) of ( ) | Control Body Wt. Change | Animal Wt. Diff.(T—C) | Tumor Evaluation Test | Tumor Evaluation Control | Percent T/C % |
|---|---|---|---|---|---|---|---|---|---|
| 32.0 | M | 8 | 60 | 10/10 | 1.9 | —5.0 | 14.0 | 9.0 | 155 |
| 16.0 | M | 8 | 60 | 9/10 | 1.9 | —5.5 | 15.0 | 9.0 | 166 |
| 8.00 | M | 8 | 60 | 10/10 | 1.9 | —4.8 | 12.5 | 9.0 | 138 |
| 0.00 | M | 8 | 60 | 10/10 | 1.9 | — .9 | 10.0 | 9.0 | 111 |
| 128 | M | 24 | 60 | 10/10 | 1.9 | —6.5 | 11.5 | 9.0 | 127 |
| 64.0 | M | 24 | 60 | 9/10 | 1.9 | —6.2 | 13.0 | 9.0 | 144 |
| 32.0 | M | 24 | 60 | 10/10 | 1.9 | —5.2 | 18.0 | 9.0 | 200 |
| 16.0 | M | 24 | 60 | 10/10 | 1.9 | —5.0 | 17.0 | 9.0 | 188 |
| 8.00 | M | 24 | 60 | 10/10 | 1.9 | —4.4 | 14.0 | 9.0 | 155 |
| 4.00 | M | 24 | 60 | 10/10 | 1.9 | —4.6 | 9.5 | 9.0 | 105 |
| 0.00 | M | 24 | 60 | 10/10 | 1.9 | —1.3 | 11.0 | 9.0 | 122 |
| 128 | M | 16 | 60 | 10/10 | 1.9 | —5.7 | 11.0 | 9.0 | 122 |
| 64.0 | M | 16 | 60 | 10/10 | 1.9 | —6.1 | 13.5 | 9.0 | 150 |
| 32.0 | M | 16 | 60 | 10/10 | 1.9 | —5.1 | 18.0 | 9.0 | 200 |
| 16.0 | M | 16 | 60 | 10/10 | 1.9 | —4.8 | 16.0 | 9.0 | 177 |
| 8.00 | M | 16 | 60 | 10/10 | 1.9 | —5.8 | 13.0 | 9.0 | 144 |
| 4.00 | M | 16 | 60 | 10/10 | 1.9 | —5.0 | 12.5 | 9.0 | 138 |
| 0.00 | M | 16 | 60 | 10/10 | 1.9 | — .9 | 9.0 | 9.0 | 100 |
| 512 | M | 1 | 30 | 8/8 | .5 | — .7 | 19.1 | 10.6 | 180 |
| 256 | M | 1 | 30 | 7/8 | .5 | —5.9 | 18.6 | 10.6 | 175 |
| 128 | M | 1 | 30 | 8/8 | .5 | —2.9 | 16.3 | 10.6 | 153 |
| 64.0 | M | 1 | 30 | 8/8 | .5 | —1.7 | 12.8 | 10.6 | 120 |
| 64.0 | Q | 1 | 30 | 0/8 | .5 | — .5 | 2.1 | 10.6 | — |
| 32.0 | Q | 1 | 30 | 0/8 | .5 | — .5 | 2.8 | 10.6 | — |
| 16.0 | Q | 1 | 30 | 5/8 | .5 | —1.8 | 8.9 | 10.6 | — |
| 8.00 | Q | 1 | 30 | 3/8 | .5 | .2 | 3.4 | 10.6 | — |
| 4.00 | Q | 1 | 30 | 5/8 | .5 | —1.5 | 8.7 | 10.6 | — |
| 2.00 | Q | 1 | 30 | 5/8 | .5 | —2.0 | 29.8 | 10.6 | — |
| 128 | R | 1 | 30 | 0/8 | .5 | — .5 | 2.1 | 10.6 | — |
| 64.0 | R | 1 | 30 | 2/8 | .5 | 6.3 | 3.4 | 10.6 | — |
| 32.0 | R | 1 | 30 | 7/8 | .5 | —2.7 | 11.8 | 10.6 | 111 |
| 16.0 | R | 1 | 30 | 7/8 | .5 | —3.8 | 11.0 | 10.6 | 103 |
| 8.00 | R | 1 | 30 | 7/8 | .5 | —2.7 | 10.6 | 10.6 | 100 |
| 4.00 | R | 1 | 30 | 8/8 | .5 | — .9 | 10.8 | 10.6 | 101 |
| 512 | Q | 1 | 30 | 3/8 | .5 | 1.7 | 3.0 | 10.6 | — |
| 256 | Q | 1 | 30 | 7/8 | .5 | 1.6 | 9.3 | 10.6 | 87 |
| 128 | Q | 1 | 30 | 8/8 | .5 | 2.1 | 10.3 | 10.6 | 97 |
| 64.0 | Q | 1 | 30 | 7/8 | .5 | —2.5 | 10.9 | 10.6 | 102 |
| 32.0 | Q | 1 | 30 | 8/8 | .5 | 1.7 | 11.0 | 10.6 | 103 |
| 16.0 | Q | 1 | 30 | 8/8 | .5 | 2.8 | 10.3 | 10.6 | 97 |
| 512 | R | 1 | 30 | 5/8 | .5 | — .6 | 9.8 | 10.6 | 97 |
| 256 | R | 1 | 30 | 8/8 | .5 | 2.3 | 10.0 | 10.6 | 94 |
| 128 | R | 1 | 30 | 7/8 | .5 | .2 | 10.1 | 10.6 | 95 |
| 64.0 | R | 1 | 30 | 8/8 | .5 | 1.6 | 11.0 | 10.6 | 103 |
| 32.0 | R | 1 | 30 | 6/8 | .5 | 2.4 | 10.6 | 10.6 | 100 |
| 16.0 | R | 1 | 30 | 7/8 | .5 | 1.8 | 10.6 | 10.6 | 100 |

C = Acetone,
2 = saline,
T = Saline with Tween,
M = Hydroxypropylcellulose (HPC),
Q = Citric Acid,
R = Lactic Acid,

EXAMPLE 2

N,N'-Bis-(6-amino)-4,4-hexamethylene-diaminoquinaldine was evaluated against the L-1210 Lymphoid leukemia in CDF₁ mice following the procedure of Example 1. The data are summarized in Table II.

Table II

Activity of N,N'-Bis-(6:amino)-4,4-Hexamethylene-Diaminoquinaldine Against L-1210 Lymphoid Leukemia in CDF₁ Mice

| Dose (i.p.) | Vehicle | No.of Injec. | Day of Eval. | Survivors ( ) of ( ) | Control Body Wt. Change | Animal Wt. Diff.(T—C) | Tumor Evaluation Test | Tumor Evaluation Control | Percent T/C % |
|---|---|---|---|---|---|---|---|---|---|
| 9.00 | 2 | 9 | 30 | 6/6 | .9 | .6 | 10.8 | 8.9 | 121 |
| 4.50 | 2 | 9 | 30 | 6/6 | .9 | .3 | 9.8 | 8.9 | 110 |
| 2.25 | 2 | 9 | 30 | 6/6 | .9 | .5 | 9.8 | 8.9 | 110 |
| 400 | 2 | 3 | 30 | 6/6 | 1.5 | —4.9 | 12.8 | 8.6 | 148 |
| 200 | 2 | 3 | 30 | 6/6 | 1.5 | —1.9 | 11.0 | 8.6 | 127 |
| 100 | 2 | 3 | 30 | 6/6 | 1.5 | —1.4 | 9.7 | 8.6 | 112 |
| 300 | T | 3 | 20 | 6/6 | 1.1 | —3.3 | 9.0 | 8.9 | 101 |
| 200 | T | 3 | 20 | 6/6 | 1.1 | —3.2 | 11.7 | 8.9 | 131 |
| 133 | T | 3 | 20 | 5/6 | 1.1 | —1.0 | 11.2 | 8.9 | 125 |
| 300 | T | 9 | 30 | 0/6 | 1.0 | —1.0 | 0.0 | 8.5 | — |
| 150 | T | 9 | 30 | 5/6 | 1.0 | —4.0 | 14.3 | 8.5 | 168 |
| 75.0 | T | 9 | 30 | 6/6 | 1.0 | —4.7 | 11.8 | 8.5 | 138 |
| 37.5 | T | 9 | 30 | 6/6 | 1.0 | —2.8 | 12.8 | 8.5 | 150 |
| 400 | 2 | 3 | 30 | 6/6 | 1.5 | —4.9 | 12.8 | 8.6 | 148 |
| 200 | 2 | 3 | 30 | 6/6 | 1.5 | —1.9 | 11.0 | 8.6 | 127 |
| 100 | 2 | 3 | 30 | 6/6 | 1.5 | —1.4 | 9.7 | 8.6 | 112 |
| 300 | T | 3 | 20 | 6/6 | 1.1 | —3.3 | 9.0 | 8.9 | 101 |
| 200 | T | 3 | 20 | 6/6 | 1.1 | —3.2 | 11.7 | 8.9 | 131 |

Table II-continued

Activity of N,N'-Bis-(6:amino)-4,4-Hexamethylene-Diaminoquinaldine Against L-1210 Lymphoid Leukemia in CDF₁ Mice

| Dose (i.p.) | Vehicle | No.of Injec. | Day of Eval. | Survivors ( ) of ( ) | Control Body Wt. Change | Animal Wt. Diff.(T−C) | Tumor Evaluation Test | Tumor Evaluation Control | Percent T/C % |
|---|---|---|---|---|---|---|---|---|---|
| 133 | T | 3 | 20 | 5/6 | 1.1 | −1.0 | 11.2 | 8.9 | 125 |
| 300 | T | 9 | 30 | 0/6 | 1.0 | −1.0 | 0.0 | 8.5 | — |
| 150 | T | 9 | 30 | 5/6 | 1.0 | −4.0 | 14.3 | 8.5 | 168 |
| 75.0 | T | 9 | 30 | 6/6 | 1.0 | −4.7 | 11.8 | 8.5 | 138 |
| 37.5 | T | 9 | 30 | 6/6 | 1.0 | −2.8 | 12.8 | 8.5 | 150 |
| 400 | 2 | 3 | 30 | 6/6 | 1.5 | −4.9 | 12.2 | 8.6 | 148 |
| 200 | 2 | 3 | 30 | 6/6 | 1.5 | −1.9 | 11.0 | 8.6 | 127 |
| 100 | 2 | 3 | 30 | 6/6 | 1.5 | −1.4 | 9.7 | 8.6 | 112 |
| 300 | T | 3 | 20 | 6/6 | 1.1 | −3.3 | 9.0 | 8.9 | 101 |
| 200 | T | 3 | 20 | 6/6 | 1.1 | −3.2 | 11.7 | 8.9 | 131 |
| 133 | T | 3 | 20 | 5/6 | 1.1 | −1.0 | 11.2 | 8.9 | 125 |
| 400 | 2 | 3 | 30 | 6/6 | 1.5 | −4.9 | 12.8 | 8.6 | 148 |
| 200 | 2 | 3 | 30 | 6/6 | 1.5 | −1.9 | 11.0 | 8.6 | 127 |
| 100 | 2 | 3 | 30 | 6/6 | 1.5 | −1.4 | 9.7 | 8.6 | 112 |
| 9.00 | 2 | 9 | 30 | 6/6 | .9 | .6 | 10.8 | 8.9 | 121 |
| 4.50 | 2 | 9 | 30 | 6/6 | .9 | .3 | 9.8 | 8.9 | 110 |
| 2.25 | 2 | 9 | 30 | 6/6 | .9 | .5 | 9.8 | 8.9 | 110 |
| 400 | 2 | 3 | 30 | 6/6 | 1.5 | −4.9 | 12.8 | 8.6 | 148 |
| 200 | 2 | 3 | 30 | 6/6 | 1.5 | −1.9 | 11.0 | 8.6 | 127 |
| 100 | 2 | 3 | 30 | 6/6 | 1.5 | −1.4 | 9.7 | 8.6 | 112 |
| 300 | T | 3 | 20 | 6/6 | 1.1 | −3.3 | 9.0 | 8.9 | 101 |
| 200 | T | 3 | 20 | 6/6 | 1.1 | −3.2 | 11.7 | 8.9 | 131 |
| 133 | T | 3 | 20 | 5/6 | 1.1 | −1.0 | 11.2 | 8.9 | 125 |
| 300 | T | 9 | 30 | 0/6 | 1.0 | −1.0 | 0.0 | 8.5 | — |
| 150 | T | 9 | 30 | 5/6 | 1.0 | −4.0 | 14.3 | 8.5 | 168 |
| 75.0 | T | 9 | 30 | 6/6 | 1.0 | −4.7 | 11.8 | 8.5 | 138 |
| 37.5 | T | 9 | 30 | 6/6 | 1.0 | −2.8 | 12.8 | 8.5 | 150 |
| 400 | 2 | 3 | 30 | 6/6 | 1.5 | −4.9 | 12.8 | 8.6 | 148 |
| 200 | 2 | 3 | 30 | 6/6 | 1.5 | −1.9 | 11.0 | 8.6 | 127 |
| 100 | 2 | 3 | 30 | 6/6 | 1.5 | −1.4 | 9.7 | 8.6 | 112 |

C = Acetone,
2 = Saline,
T = Saline with Tween,
M = Hydroxypropylcellulose (HPC),
D = Alcohol,
J = Methylcellulose

EXAMPLE 3

N,N'-Bis-(6-Amino)-4,4-hexamethylene-diaminoquinaldine was evaluated against P 388 Lymphocytic leukemia in BDF₁ mice following the procedure of Example 1. The data are summarized in Table III:

Table III

Activity of N,N'-Bis-(6-Amino)-4,4-Hexamethylene-Diaminoquinaldine Against P 388 Lymphocytic Leukemia in BDF₁ Mice

| Dose (i.p.) | Vehicle | No. of Injec. | Day of Eval. | Survivors ( ) of ( ) | Control Body Wt. Change | Animal Wt. Diff.(T−C) | Tumor Evaluation Test | Tumor Evaluation Control | Percent T/C % |
|---|---|---|---|---|---|---|---|---|---|
| 400 | 2 | 3 | 30 | 6/6 | 1.4 | −5.5 | 25.0 | 10.0 | 250 |
| 300 | 2 | 3 | 30 | 6/6 | 1.4 | −4.0 | 23.0 | 10.0 | 230 |
| 200 | 2 | 3 | 30 | 6/6 | 1.4 | −3.1 | 21.0 | 10.0 | 210 |
| 400 | M | 3 | 30 | 6/6 | .9 | −5.1 | 28.0 | 11.0 | 254 |
| 300 | M | 3 | 30 | 6/6 | .9 | −5.6 | 7.0 | 11.0 | — |
| 198 | M | 3 | 30 | 6/6 | .9 | −4.7 | 23.5 | 11.0 | 213 |
| 400 | 2 | 3 | 30 | 6/6 | 1.4 | −5.5 | 25.0 | 10.0 | 250 |
| 300 | 2 | 3 | 30 | 6/6 | 1.4 | −4.0 | 23.0 | 10.0 | 230 |
| 200 | 2 | 3 | 30 | 6/6 | 1.4 | −3.1 | 21.0 | 10.0 | 210 |
| 400 | M | 3 | 30 | 6/6 | .9 | −5.1 | 28.0 | 11.0 | 254 |
| 300 | M | 3 | 30 | 6/6 | .9 | −5.6 | 7.0 | 11.0 | — |
| 198 | M | 3 | 30 | 6/6 | .9 | −4.7 | 23.5 | 11.0 | 213 |
| 300 | 2 | 3 | 30 | 6/6 | 2.1 | −3.1 | 23.5 | 11.0 | 213 |
| 150 | 2 | 3 | 30 | 6/6 | 2.1 | −3.3 | 24.0 | 11.0 | 218 |
| 75.0 | 2 | 3 | 30 | 6/6 | 2.1 | − .4 | 17.5 | 11.0 | 159 |
| 37.5 | 2 | 3 | 30 | 6/6 | 2.1 | − .9 | 18.0 | 11.0 | 163 |
| 400 | 2 | 3 | 30 | 6/6 | 1.4 | −5.5 | 25.0 | 10.0 | 250 |
| 300 | 2 | 3 | 30 | 6/6 | 1.4 | −4.0 | 23.0 | 10.0 | 230 |
| 200 | 2 | 3 | 30 | 6/6 | 1.4 | −3.1 | 21.0 | 10.0 | 210 |
| 400 | M | 3 | 30 | 6/6 | .9 | −5.1 | 28.0 | 11.0 | 254 |
| 300 | M | 3 | 30 | 6/6 | .9 | −5.6 | 7.0 | 11.0 | — |
| 198 | M | 3 | 30 | 6/6 | .9 | −4.7 | 23.5 | 11.0 | 213 |
| 300 | 2 | 3 | 30 | 6/6 | 2.1 | −3.1 | 23.5 | 11.0 | 213 |
| 150 | 2 | 3 | 30 | 6/6 | 2.1 | −3.3 | 24.0 | 11.0 | 218 |
| 75.0 | 2 | 3 | 30 | 6/6 | 2.1 | − .4 | 17.5 | 11.0 | 159 |
| 37.5 | 2 | 3 | 30 | 6/6 | 2.1 | − .9 | 18.0 | 11.0 | 163 |
| 18.7 | 2 | 3 | 30 | 6/6 | 2.0 | −1.5 | 16.5 | 11.0 | 150 |
| 9.38 | 2 | 3 | 30 | 6/6 | 2.0 | − .3 | 14.0 | 11.0 | 127 |
| 4.69 | 2 | 3 | 30 | 6/6 | 2.0 | − .7 | 12.0 | 11.0 | 109 |
| 400 | 2 | 3 | 30 | 6/6 | 1.4 | −5.5 | 25.0 | 10.0 | 250 |
| 300 | 2 | 3 | 30 | 6/6 | 1.4 | −4.0 | 23.0 | 10.0 | 230 |

Table III-continued

Activity of N,N'-Bis-(6-Amino)-4,4-Hexamethylene-Diaminoquinaldine Against P 388 Lymphocytic Leukemia in BDF$_1$ Mice

| Dose (i.p.) | Vehicle | No. of Injec. | Day of Eval. | Survivors ( ) of ( ) | Control Body Wt. Change | Animal Wt. Diff.(T—C) | Tumor Evaluation Test | Tumor Evaluation Control | Percent T/C % |
|---|---|---|---|---|---|---|---|---|---|
| 200 | 2 | 3 | 30 | 6/6 | 1.4 | −3.1 | 21.0 | 10.0 | 210 |

M = Hydroxypropylcellulose (HPC),
2 = Saline

EXAMPLE 4

N,N-Bis-(6-amino)-4,4-hexamethylene-diaminoquinaldine was evaluated against P 388 Lymphocytic leukemia in CDF$_1$ rats following the procedure of Example 1. The data are summarized in Table IV:

Table IV

Activity of N,N'Bis-(6-Amino)-4,4-Hexamethylene-Diaminoquinaldine Against P 388 Lymphocytic Leukemia in CDF$_1$ Mice

| Dose (i.p.) | Vehicle | No.of Injec. | Day of Eval. | Survivors ( ) of ( ) | Control Body Wt. Change | Animal Wt. Diff.(T—C) | Tumor Evaluation Test | Tumor Evaluation Control | Percent T/C % |
|---|---|---|---|---|---|---|---|---|---|
| 300 | D | 3 | 30 | 6/6 | .7 | −3.4 | 21.0 | 11.0 | 190 |
| 150 | D | 3 | 30 | 6/6 | .7 | −4.0 | 20.5 | 11.0 | 186 |
| 75.0 | D | 3 | 30 | 6/6 | .7 | − .6 | 19.5 | 11.0 | 177 |
| 300 | D | 3 | 30 | 6/6 | .7 | −3.4 | 21.0 | 11.0 | 190 |
| 150 | D | 3 | 30 | 6/6 | .7 | −4.0 | 20.5 | 11.0 | 186 |
| 75.0 | D | 3 | 30 | 6/6 | .7 | − .6 | 19.5 | 11.0 | 177 |
| 300 | D | 3 | 30 | 6/6 | .7 | −3.4 | 21.0 | 11.0 | 190 |
| 150 | D | 3 | 30 | 6/6 | .7 | −4.0 | 20.5 | 11.0 | 186 |
| 75.0 | D | 3 | 30 | 6/6 | .7 | − .6 | 19.5 | 11.0 | 177 |
| 300 | D | 3 | 30 | 6/6 | .7 | −3.4 | 21.0 | 11.0 | 190 |
| 150 | D | 3 | 30 | 6/6 | .7 | −4.0 | 20.5 | 11.0 | 186 |
| 75.0 | D | 3 | 30 | 6/6 | .7 | − .6 | 19.5 | 11.0 | 177 |
| 300 | D | 3 | 30 | 6/6 | .7 | −3.4 | 21.0 | 11.0 | 190 |
| 150 | D | 3 | 30 | 6/6 | .7 | −4.0 | 20.5 | 11.0 | 186 |
| 75.0 | D | 3 | 30 | 6/6 | .7 | − .6 | 19.5 | 11.0 | 177 |

D = Alcohol

EXAMPLE 5

A minimum reproducable tumor inhibition of test over controls resulting in a T/C ≤ 42% is considered significant. N,N-Bis-(6-amino)-4,4-hexamethylene-diaminoquinaldine dihydrochloride was evaluated against B16 melanocarcinoma in BDF$_1$ mice following the procedure of Example 1. The data are summarized in Table V.

Table V

Activity of N,N'Bis-(6-Amino)-4,4-Hexamethylene-Diaminoquinaldine Against B16 Melanocarcinoma In Mice

| Dose (i.p.) | Vehicle | No.of Injec. | Day of Eval. | Survivors ( ) of ( ) | Control Body Wt. Change | Animal Wt. Diff.(T—C) | Tumor Evaluation Test | Tumor Evaluation Control | Percent T/C % |
|---|---|---|---|---|---|---|---|---|---|
| 300 | T | 9 | 45 | 6/6 | 1.6 | −5.0 | 7.0 | 16.0 | — |
| 150 | T | 9 | 45 | 5/6 | 1.6 | −5.3 | 8.0 | 16.0 | — |
| 75.0 | T | 9 | 45 | 6/6 | 1.6 | −3.2 | 15.0 | 16.0 | 93 |
| 37.5 | T | 9 | 45 | 6/6 | 1.6 | −3.4 | 17.5 | 16.0 | 109 |
| 18.7 | T | 9 | 45 | 6/6 | 1.6 | −1.1 | 15.5 | 16.0 | 96 |

T = Saline with Tween-80

EXAMPLE 6

N,N-Bis-(6-amino)-4,4-hexamethylene-diaminoquinaldine was evaluated against Lewis Lung carcinoma in (57BL/6) mice following the process of Example 1. The data are summarized in Table VI.

Table VI

Activity of N,N'-Bis-(6-Amino)-4,4-Hexamethylene-Diaminoquinaldine Against Lewis Lung Carcinoma (57BL/6) Mice

| Dose (i.p.) | Vehicle | No.of Injec. | Day of Eval. | Survivors ( ) of ( ) | Control Body Wt. Change | Animal Wt. Diff.(T—C) | Tumor Evaluation Test | Tumor Evaluation Control | Percent T/C % |
|---|---|---|---|---|---|---|---|---|---|
| 300 | M | 9 | 12 | 1/10 | 3.2 | −8.7 | 63 | 1904 | — |
| 150 | M | 9 | 12 | 6/10 | 3.2 | −7.2 | 221 | 1904 | — |
| 75.0 | M | 9 | 12 | 10/10 | 3.2 | −5.2 | 531 | 1904 | 27 |
| 37.5 | M | 9 | 12 | 9/10 | 3.2 | −3.6 | 1029 | 1904 | 54 |
| 18.7 | M | 9 | 12 | 10/10 | 3.2 | −1.9 | 1437 | 1904 | 75 |
| 600 | M | 9 | 12 | 8/10 | 3.2 | −1.7 | 1587 | 1904 | 83 |
| 300 | M | 9 | 12 | 9/9 | 3.2 | − .6 | 1606 | 1904 | 84 |
| 150 | M | 9 | 12 | 9/9 | 3.2 | − .2 | 1944 | 1904 | 102 |
| 75.0 | M | 9 | 12 | 9/9 | 3.2 | − .2 | 1960 | 1904 | 102 |
| 37.5 | M | 9 | 12 | 8/8 | 3.2 | − .1 | 1727 | 1904 | 90 |
| 300 | M | 9 | 60 | 10/10 | 1.0 | −4.9 | 10.0 | 23.0 | — |
| 150 | M | 9 | 60 | 10/10 | 1.0 | −4.1 | 15.5 | 23.0 | — |

Table VI-continued

Activity of N,N'-Bis-(6-Amino)-4,4-Hexamethylene-Diaminoquinaldine Against Lewis Lung Carcinoma (57BL/6) Mice

| Dose (i.p.) | Vehicle | No.of Injec. | Day of Eval. | Survivors ( ) of ( ) | Control Body Wt. Change | Animal Wt. Diff.(T–C) | Tumor Evaluation Test | Tumor Evaluation Control | Percent T/C % |
| --- | --- | --- | --- | --- | --- | --- | --- | --- | --- |
| 75.0 | M | 9 | 60 | 10/10 | 1.0 | −3.2 | 25.5 | 23.0 | 110 |
| 37.5 | M | 9 | 60 | 10/10 | 1.0 | −3.4 | 31.5 | 23.0 | 136 |
| 18.7 | M | 9 | 60 | 10/10 | 1.0 | −1.6 | 33.0 | 23.0 | 143 |
| 600 | M | 9 | 60 | 9/9 | 1.0 | − .8 | 30.0 | 23.0 | 130 |
| 300 | M | 9 | 60 | 10/10 | 1.0 | − .4 | 29.0 | 23.0 | 126 |
| 150 | M | 9 | 60 | 9/9 | 1.0 | .2 | 29.0 | 23.0 | 126 |
| 75.0 | M | 9 | 60 | 9/9 | 1.0 | .0 | 23.0 | 23.0 | 100 |
| 37.5 | M | 9 | 60 | 8/8 | 1.0 | − .2 | 29.0 | 23.0 | 126 |

M = Klucel (hydroxypropylcellulose) (HPC)

The compounds useful in the practice of this invention can be prepared in various preparations suitable for parenteral administration including sterile aqueous or non-aqueous solutions, suspensions or emulsions according to methods well known in the art. Examples of suitable non-aqueous solvents or vehicles include propylene glycol, ethyl oleate, methylcellulose and the like. Such dosage forms may also contain adjuvants such as preserving, wetting, emulsifying and dispersing agents. They may be sterilized by, for example, filtration through a bacterial retaining filter, by incorporating sterilizing agents into the composition or by irradiation or heating. They can also be manufactured in the form of sterile solid compositions which can be dissolved in sterile water, or some other sterile injectable medium immediately before use.

The following example further illustrates one embodiment of this invention:

EXAMPLE 7

Sterile ampoules are prepared by methods well known in the art containing 100 mg. of N,N-Bis-(6-amino)4,4-hexamethylene-diaminoquinaldine in 100 mg. of distilled water.

I claim:

1. A method of prolonging the survival time of a mammalian L-1210 lymphoid and P388 lymphocytic leukemia cancer host comprising administering 30-600 mg-kg body weight of the compound N,N'-bis-(6-amino)-4,4-hexamehtylenediamino quinaldine or a pharmaceutically acceptable acid addition salt thereof to said host.

2. The method of claim 1 wherein the compound is administered as the dihydrochloride salt.

3. The method of claim 2 wherein said compound is administered to said host in dosages of from 30 to 600 mg./kg. of body weight daily.

* * * * *